United States Patent [19]

Tadych

[11] Patent Number: 5,281,221

[45] Date of Patent: Jan. 25, 1994

[54] ANTIMICROBIAL DEVICE FOR USE IN EXTERNAL FIXATORS

[76] Inventor: Kevin L. Tadych, 311 Elm St., P.O. Box 1176, Woodruff, Wis. 54568

[21] Appl. No.: 622,562

[22] Filed: Dec. 5, 1990

[51] Int. Cl.⁵ .............................................. A61F 5/04
[52] U.S. Cl. ......................................... 606/53; 606/59
[58] Field of Search ................... 606/59, 54, 55, 56, 606/57, 58, 60, 53

[56] References Cited

U.S. PATENT DOCUMENTS

| | | | |
|---|---|---|---|
| 2,035,952 | 3/1936 | Ettinger | 606/56 |
| 2,055,024 | 9/1936 | Bittner | 606/56 |
| 2,391,693 | 12/1945 | Ettinger | 606/57 |
| 2,398,915 | 4/1946 | Bell | 606/59 |
| 3,809,074 | 5/1974 | De Moude | 606/59 |
| 4,185,624 | 1/1980 | Gentile | 606/59 |
| 4,258,708 | 3/1981 | Gentile | 606/59 |
| 4,662,365 | 5/1987 | Gotzen | 606/59 |
| 4,856,504 | 8/1989 | Yamamoto | 128/888 |
| 4,890,631 | 1/1990 | Hardy | 606/59 |
| 4,957,495 | 9/1990 | Kluger | 606/59 |

Primary Examiner—Michael A. Brown
Attorney, Agent, or Firm—Paul R. Puerner

[57] ABSTRACT

An external fixator is provided with an antimicrobial device that greatly reduces the probability of infection around the fixator pins. The antimicrobial device comprises a sleeve that is pressed with an interference fit over each pin after the pin is installed in the patient. A cuff of Dacron felt surrounds the sleeve and is located within the subcutaneous tissue of the patient. The interference fit between the pin and the sleeve prevents entry of bacteria into the subcutaneous tissue between the sleeve and pin. The Dacron felt promotes ingrowth of scar tissue into the cuff interstices, thereby utilizing the body's natural defenses against infection. The external fixator frame is assembled to the pins after the antimicrobial devices are in place.

4 Claims, 1 Drawing Sheet

ANTIMICROBIAL DEVICE FOR USE IN EXTERNAL FIXATORS

BACKGROUND OF THE INVENTION

1. Field of the Invention

This invention pertains to medical equipment, and more particularly to apparatus used in orthopedic surgery.

2. Description of the Prior Art

External fixators for stabilizing fractured or osteotomized bones are well known. Such fixators immobilize damaged bones and thus aid natural healing processes to repair the bones.

In the use of external fixators, threaded metal pins are screwed into appropriately tapped holes located on opposite sides of the bone fracture. The pins protrude through the muscle, subcutaneous tissue, and skin. A frame is assembled to the exposed ends of the pins to join them together. The fixator frame rigidly retains the pins and thus the associated bones in place while healing occurs. Typical external fixators may be seen in U.S. Pat. Nos. 4,127,119 and 4,620,533.

Because biological tissue does not adhere to the metal fixator pins, a chronic break remains in the skin around the pins. As a result, a rather common complication involving external fixators is infection that occurs around the pins. Investigations have shown that infections occur in about 10% of the pins used in external fixators. The infections range from superficial skin infection to deep bone infection, i.e., osteomyelitis.

The primary treatment for external fixator pin infections is antibiotics. However, antibiotics are often ineffective. In those situations, it is necessary to remove the pins and place them at new sites. In severe cases, use of the external fixator must be terminated.

U.S. Pat. No. 4,856,504 describes antimicrobial wound dressing and skin fixator for orthopedic pins that includes an annular patch containing an antimicrobial agent. The patch is placed over an orthopedic pin and against the skin. The patch is held in place by a pad of pressure-sensitive adhesive. A flange overlies the patch and pad, and the flange is secured to the fixator pin. Although the antimicrobial patch of the 4,856,504 patent is helpful for preventing infection around a pin, it does not contribute to the natural ingrowth of tissue around the pin so as to bring into play the natural defenses of the body to bacterial infection.

Thus, a need exists for improvements in the prevention of infections associated with external fixators.

SUMMARY OF THE INVENTION

In accordance with the present invention, an antimicrobial device is provided that more effectively prevents infections in orthopedic external fixators than was previously possible. This is accomplished by apparatus that includes a sleeve pressed onto each pin of an external fixator and a cuff that surrounds a portion of the sleeve.

The external fixators with which the present invention is used may be generally conventional, having known pins with threaded first ends. The fixator frame that rigidly joins the second ends of the fixator pins to each other may also be conventional.

The sleeve of the antimicrobial device of the present invention comprises a short length of medical tubing having an inner diameter smaller than the outer diameter of the associated pin. The sleeve length may be approximately five centimeters.

The cuff of the antimicrobial device is preferably made of Dacron felt. The cuff is quite narrow, and it is attached circumferentially around the sleeve outer diameter.

After a fixator pin is installed in the bone of a patient in the usual manner, an antimicrobial device according to the present invention is pressed over the pin. The relative sizes of the pin outer diameter and sleeve inner diameter produce an interference fit between the sleeve and pin. The sleeve length is sufficient to extend from the region of the patient's subcutaneous tissue to outside of the skin. The sleeve is positioned on the pin such that the cuff is located in the subcutaneous tissue adjacent to the dermis.

After the antimicrobial devices are in place over their associated fixated pins, the fixator frame is assembled to the exposed ends of the pins in the normal manner. After adjusting the fixator frame, the external fixator rigidly retains the bone segments immobile for healing.

The interference fit between the pins and their respective sleeves prevents entry of bacteria pathogens into the tissue around the pins. At the same time, the Dacron cuff promotes ingrowth of scar tissue into the interstices of the cuff, thereby partially restoring the primary barrier against entry of the pathogens into the body. As an added measure of protection, the cuff may be impregnated with antibiotics.

Other advantages, benefits, and features of the invention will become apparent to those skilled in the art upon reading the detailed description of the invention.

DETAILED DESCRIPTION OF THE INVENTION

Figure 2:
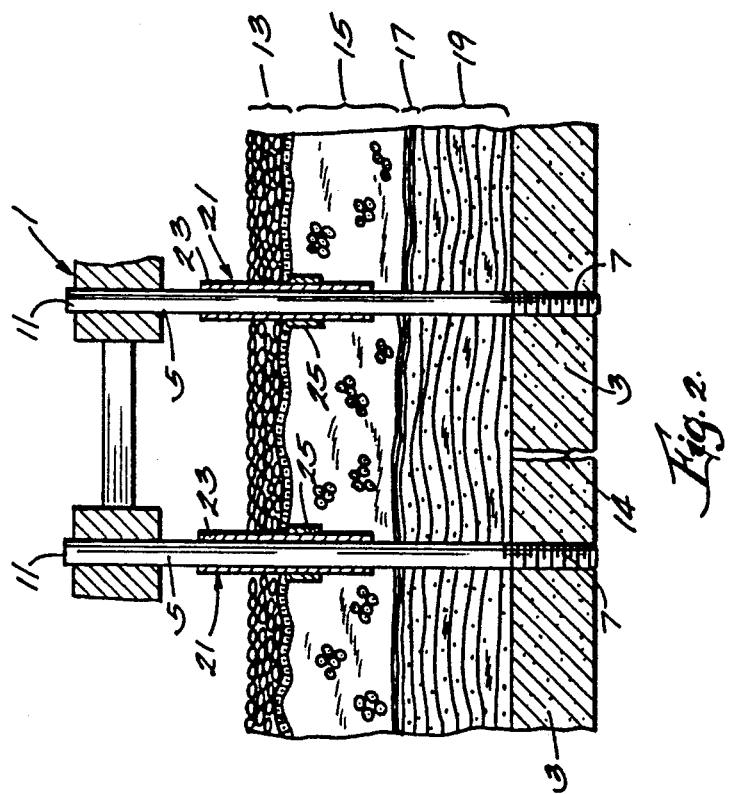
FIG. 2 is a cross-sectional view of the external fixator and antimicrobial device installed in a patient.
Figure 1:
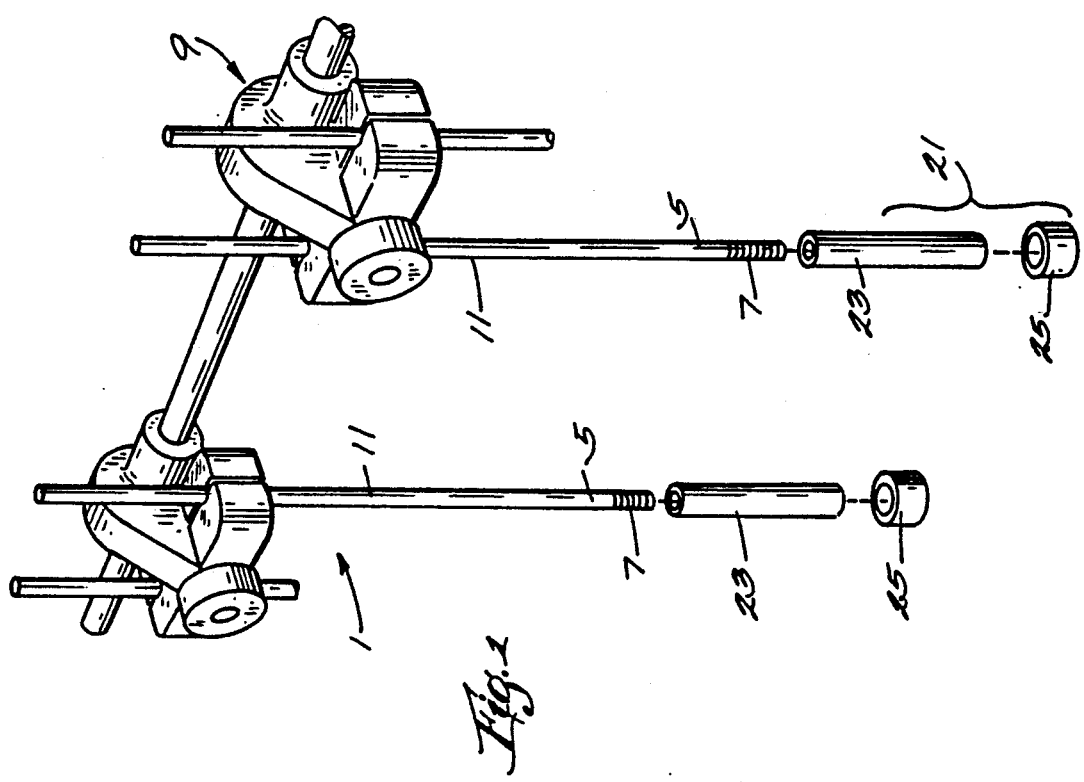
FIG. 1 is an exploded perspective view of a portion of an external fixator in conjunction with the antimicrobial device of the present invention.

Referring to FIGS. 1 and 2, an external fixator 1 is illustrated that includes the present invention. The external fixator is used in orthopedic surgery for stabilizing a fractured bone 3. However, it will be understood that the invention is not limited to use with external fixators.

The external fixator 1 is shown as comprising a pair of elongated pins 5, each having threads 7 on one end thereof. The fixator pins 5 are commercially available in different lengths and diameters to suit different orthopedic requirements. For example, the diameters of standard pins range from 1 millimeter to 6.5 millimeters. A fixator frame 9 is adjustably assemblable to the second ends 11 of the pins 5.

To install the external fixator 1, the skin 13 is incised on opposite sides of the bone fracture 14. The subcutaneous tissue 15, deep fascia 17, and muscle 19 are dissected to the bone 3. The bone is dried and tapped to receive the threads 7 of the pins 5. The pins are chosen with a length and diameter to suit the requirements of the particular bone being set. After the pins are screwed into the tapped holes in the bone, the frame 9 is assembled to the pin ends 11 and adjusted to rigidly retain the bones in place until the fracture 14 has healed.

In accordance with the present invention, an antimicrobial device 21 is incorporated onto the external fixator 1. The antimicrobial device 21 comprises a sleeve 23 and a cuff 25 in association with each pin 5 of the external fixator. In the preferred embodiment, the sleeve 23 is manufactured from a medical grade tubing formulated from silicon elastomers. A tubing marketed under the trademark SYLASTIC works very well. The sleeve is designed with an inner diameter that is slightly smaller than the outer diameter of the particular pin with which it is used. For instance, the sleeve to be used with a 5 millimeter diameter pin has an inner diameter of 4.8 millimeters. A sleeve length of approximately 5 centimeters is satisfactory for most applications.

The cuff 25 of each antimicrobial device 21 is preferably manufactured from a Dacron felt. The cuff has an inner diameter that fits snugly around the outer diameter of the associated sleeve 23. The cuff length may be between approximately 3 millimeters and 5 millimeters. The cuff is preferably bonded to the sleeve outer diameter at approximately the mid-point thereof. Bonding may be achieved by use of an adhesive such as SYLASTIC Medical Adhesive Type A.

When using the antimicrobial device 21 with an external fixator 1, the two sites for the fixator pins 5 are prepared in the usual manner, and the appropriate pins are screwed into the bone 3. Then the properly sized sleeve 23 of an antimicrobial device is pressed over a pin until the cuff 25 is at the level of the subcutaneous tissue 15. The interference fit between the pin and the sleeve is crucial to prevent entry of bacteria along the pin and into the soft tissue underlying the skin 13. The interference fit also allows adjustable positioning of the sleeve on the pin in order to locate the cuff at the proper level and thereby accommodate the various distances encountered in different patients between the bone and the subcutaneous tissue.

After the antimicrobial devices 21 are properly positioned on the corresponding pins 5, the frame 9 is assembled to the pin free ends 11. After adjusting the frame, the external fixator 1 remains in place until the bone fracture 14 is healed.

The presence of the antimicrobial devices 21 greatly reduces the likelihood of infection at the pin sites. The medical tubing of the sleeve 23 is tolerated by human tissue, and the tubing has a low potential to incite an inflammatory response or to colonize with bacteria. Further, the antimicrobial device enables a partial restoration of the primary defense against infection by encouraging the ingrowth of scar tissue into the interstices of the cuff 25. If desired, an antibiotic agent may be added to the cuff to provide increased resistance to common bacterial pathogens.

The external fixator 1 with the antimicrobial devices 21 is removed from the patient in a generally known fashion. An elliptical incision is made around the antimicrobial device of each pin 5. The pin with the antimicrobial device pressed thereon is then screwed out of the bone 3, and the wound is closed with suture.

Thus, it is apparent that there has been provided, in accordance with the invention, an antimicrobial device for use in external fixators that fully satisfies the aims and advantages set forth above. While the invention has been described in conjunction with specific embodiments thereof, it is evident that many alternatives, modifications, and variations will be apparent to those skilled in the art in light of the foregoing description. For example, the antimicrobial device is not limited to use with external fixators 1, that rather they can be used wherever rods or pins breach the skin 13. Accordingly, it is intended to embrace all such alternatives, modifications, and variations as fall within the spirit and broad scope of the appended claims.

I claim:

1. A method of treating bone fractures comprising the steps of:
    a. providing at least a pair of pins having predetermined diameters and lengths;
    b. screwing a pin into the bone on each side of the fracture;
    c. providing an antimicrobial device in association of each pin, the antimicrobial device having a sleeve with an inner diameter slightly less than the pin diameter and a cuff that snugly surrounds the sleeve;
    d. pressing said antimicrobial device sleeve with an interference fit over each pin; and
    e. positioning the sleeve on the pin to locate the cuff in the subcutaneous tissue of the patient.

2. The method of claim 1 wherein the step of providing said antimicrobial device comprises the steps of providing said sleeve having a length of approximately five centimeters and said cuff having a length of approximately three millimeters to five millimeters.

3. The method of claim 1 comprising the further step of impregnating the cuff with an antibiotic agent.

4. The method of claim 1 wherein the step of providing said antimicrobial device comprises the step of providing said cuff made of felt material to thereby promote ingrowth of scar tissue of the subcutaneous tissue of the patient into the felt material.

* * * * *